(12) United States Patent  (10) Patent No.: US 7,776,195 B2
Kureshy et al.  (45) Date of Patent: Aug. 17, 2010

(54) INTEGRATED SAMPLE PROCESSING PLATFORM

(75) Inventors: Fareed Kureshy, Del Mar, CA (US); Vijay K. Mahant, Murrieta, CA (US); Shailendra Singh, Carlsbad, CA (US)

(73) Assignee: Autogenomics, Inc., Carlsbad, CA (US)

( * ) Notice: Subject to any disclaimer, the term of this patent is extended or adjusted under 35 U.S.C. 154(b) by 1017 days.

(21) Appl. No.: 10/513,459

(22) PCT Filed: May 28, 2003

(86) PCT No.: PCT/US03/16905

§ 371 (c)(1),
(2), (4) Date: Nov. 2, 2004

(87) PCT Pub. No.: WO03/100380

PCT Pub. Date: Dec. 4, 2003

(65) Prior Publication Data

US 2005/0233437 A1  Oct. 20, 2005

Related U.S. Application Data

(60) Provisional application No. 60/383,896, filed on May 28, 2002.

(51) Int. Cl.
*G01N 27/26* (2006.01)
(52) U.S. Cl. .......................... 204/435; 435/6
(58) Field of Classification Search ...................... None
See application file for complete search history.

(56) References Cited

U.S. PATENT DOCUMENTS

| 6,150,173 | A | 11/2000 | Schubert | |
|---|---|---|---|---|
| 6,207,031 | B1 * | 3/2001 | Adourian et al. | 204/451 |
| 6,355,423 | B1 * | 3/2002 | Rothberg et al. | 435/6 |
| 6,511,849 | B1 * | 1/2003 | Wang | 436/47 |
| 6,838,051 | B2 * | 1/2005 | Marquiss et al. | 422/63 |
| 6,875,619 | B2 * | 4/2005 | Blackburn | 506/9 |
| 2003/0186228 | A1 * | 10/2003 | McDevitt et al. | 435/6 |

FOREIGN PATENT DOCUMENTS

WO   00/66269   11/2000

* cited by examiner

*Primary Examiner*—Jeffrey S. Lundgren
(74) *Attorney, Agent, or Firm*—Fish & Associates, PC

(57) ABSTRACT

An integrated desktop analytic device comprises a fluidics station coupled to a confocal microscope detector, and a biochip is moved from the fluidics station to the detector without manual intervention of an operator.

9 Claims, 2 Drawing Sheets

INTEGRATED SAMPLE PROCESSING PLATFORM

This application is a 35 USC 371 application of international patent application with the Ser. No. PCT/US03/16905, filed May 28, 2003, which claims the benefit of U.S. provisional patent application with the Ser. No. 60/383,896, filed May 28, 2002, and which further claims the benefit of international patent application with the Ser. No. PCT/US02/17006, filed May 29, 2002, both of which are incorporated herein by reference.

FIELD OF THE INVENTION

The field of the invention is automated desktop analytic devices, especially for use in high-throughput screening.

BACKGROUND OF THE INVENTION

Recent advances in genomics and proteomics made a vast number of nucleotide and peptide sequences available for analysis, and high-throughput screening of samples for the presence and/or quantity of numerous known genes or polypeptides has gained considerable interest in recent years. While all or almost all of the individual steps or processes in high-throughput screening are well known in the art, integration of such steps or processes into a single analytic device remains a challenge. Among other difficulties and depending on the particular detection method employed, handling requirements for fluid management (e.g., sample application, hybridization, stringency washing) and detection (e.g., electronic or optical detection) are often incompatible where a single platform is employed.

For example, where binding of an analyte is electronically detected, (e.g., Nanogen's Nanochip®) various steps, including capture probe loading, analyte binding, and washing of the chip are performed in one station (e.g., Nanochip® Loader), while binding analysis is performed in a separate detector station (e.g., Nanochip® Reader). Electronic detection often allows multiple reuse of a biochip, and typically exhibits significantly accelerated analyte binding. However, due to the separation of the fluidics station and the detection station, the operator must manually transfer the chip from one station to the other, requiring proper insertion and operator control to commence detection, which at least somewhat defies the concept of automated high-throughput analysis.

Similarly, where binding of an analyte is optically detected, various biochips are commercially available as arrays of capture probes disposed on a microscope glass slide. Detection of labeled analytes that are bound to the capture probes is then performed with a flatbed scanner that typically acquires fluorescence data from the array on the surface of the slide. High-throughput analysis of such arrays is often relatively inexpensive. However, various disadvantages remain. Among other things, true signals are frequently not acquired where the surface of the glass slide is uneven. Moreover, manual operation of such slides may result in inadvertent damage to the array. Still further, fluidics management (e.g., hybridization, washing, etc.) is generally performed in one or more devices that are separate from the detector, and therefore again require user manual intervention.

To circumvent at least some of the problems associated with arrays on a glass slide, binding of the analyte may be optically detected in a chip that is disposed in a housing (e.g., Genechip by Affymetrix). A housing advantageously protects the biochip from inadvertent damage, and may further control flow of fluids (e.g., volume and/or flow control). However, such systems generally require processing the chip in a fluidics/hybridization station for binding and washing of an analyte that is bound to the capture probes, while analyte binding is detected in a separate detector. Again, an operator needs to manually insert the chip into the detector and select the suitable detection protocol prior to analysis. Furthermore, as is the case with the microscopy slide arrays, detection of the signal typically requires that fluids be completely removed from the chip to prevent quenching of the signal or other undesirable optical effects.

In another approach for high-throughput screening, multi-well plates may be used in a robotic station that automatically transfers a multi-well plate from a fluidics station to a plate reader station (see e.g., robotic stations from Beckman, Hudson, Hamilton, Gilson, Perkin Elmer, or Quiagen). Such robotic stations often integrate fluidics and detection, and employ relatively inexpensive multi-well plates. Moreover, customization of multi-well plates is generally relatively simple and can often be done using the same robotic station. However, robotic stations for multi-well plates generally have a relatively large footprint, especially where several thousand samples per day are processed. Smaller modular systems are also commercially available, however, typically fail to provide integrated sample analysis. Still further, detection of analytes in multi-well based systems is generally limited to microplate readers, which often provide limited accuracy and only perform well in assays where optical detection is not critically impaired by variations in focal depth.

Thus, although various systems for high-throughput screening are known in the art, numerous problems still remain. Therefore, there is still a need for an improved methods and systems for high-throughput screening.

SUMMARY OF THE INVENTION

The present invention is directed to an desktop analytic device for a biochip, wherein fluidics management and confocal microscope signal detection are integrated using a sample processing platform, wherein the platform serves as a basis for fluidics management, and wherein the biochip is moved along the x- and/or y-coordinate from the platform to the detector without manual user intervention.

In one aspect of the inventive subject matter, the desktop analytic device includes a substantially horizontal sample processing platform that receives a biochip that is at least partially enclosed in a housing, wherein the biochip is at least partially immersed by a fluid that is retained by the housing, wherein the biochip binds an analyte from the fluid, and wherein the fluid further comprises a non-analyte. An energy source (e.g., heater, cooling element, or ultrasound source) is functionally coupled to the platform and delivers energy to the fluid in the biochip, and a confocal microscope detector is coupled to the platform such that a substantially horizontal transport path is formed between the detector and the platform, wherein the biochip is moved in a sliding motion from the platform to the detector using the transport path. It should be especially noted that in such devices the biochip is moved within the desktop analytic device without manual intervention of an operator from the platform to the detector while the analyte is bound to the biochip, and that the sample processing platform and the detector are enclosed in the desktop analytic device.

In particularly preferred devices, movement of the biochip from the platform to the detector is caused by an actuator that pushes the biochip along at least one of an x-coordinate and a y-coordinate, and it is still further preferred that the biochip is further transported from a multi-biochip magazine to the sample processing platform within the desktop analytic device and without manual intervention of an operator (movement of the biochip from the multi-biochip magazine to the platform is preferably caused by the same actuator). Alternatively, or additionally, contemplated sample processing platform may be configured to receive a second biochip, wherein the biochip is moved from the platform to the detector while the biochip is at least partially immersed in a second fluid. A data transfer interface may further be coupled to the device and couples the desktop analytic device with a person other than the operator of the desktop analytic device (e.g., in a remote location relative to the desktop analytic device).

In another aspect of the inventive subject matter, contemplated desktop analytic devices may comprise a multi-biochip magazine, a fluidics station with a stringency platform, and confocal microscope detector, wherein a biochip is moved from the magazine via the stringency platform to the detector without manual intervention of an operator. In such devices, it is generally preferred that the multi-biochip magazine and/or the stringency platform move along a x-coordinate (e.g., via stepper motor, piezo motor, or linear motor) while the biochip is moved along a y-coordinate (e.g., via actuator).

The fluidics station in still further contemplated devices will include automatic pipette disposed within the device, wherein the pipette moves along at least one of an x-coordinate, a y-coordinate, and a z-coordinate. As already described above, it is generally preferred that the biochip is moved while the biochip is at least partially immersed in a fluid, and that the stringency platform, the multi-biochip magazine, and/or the confocal microscope detector are coupled to each other such that a portion of the stringency platform and a portion of the confocal microscope detector or multi-biochip magazine abut each other to form a transport path.

Various objects, features, aspects and advantages of the present invention will become more apparent from the following detailed description of preferred embodiments of the invention, along with the accompanying drawing.

DETAILED DESCRIPTION

Figure 1:
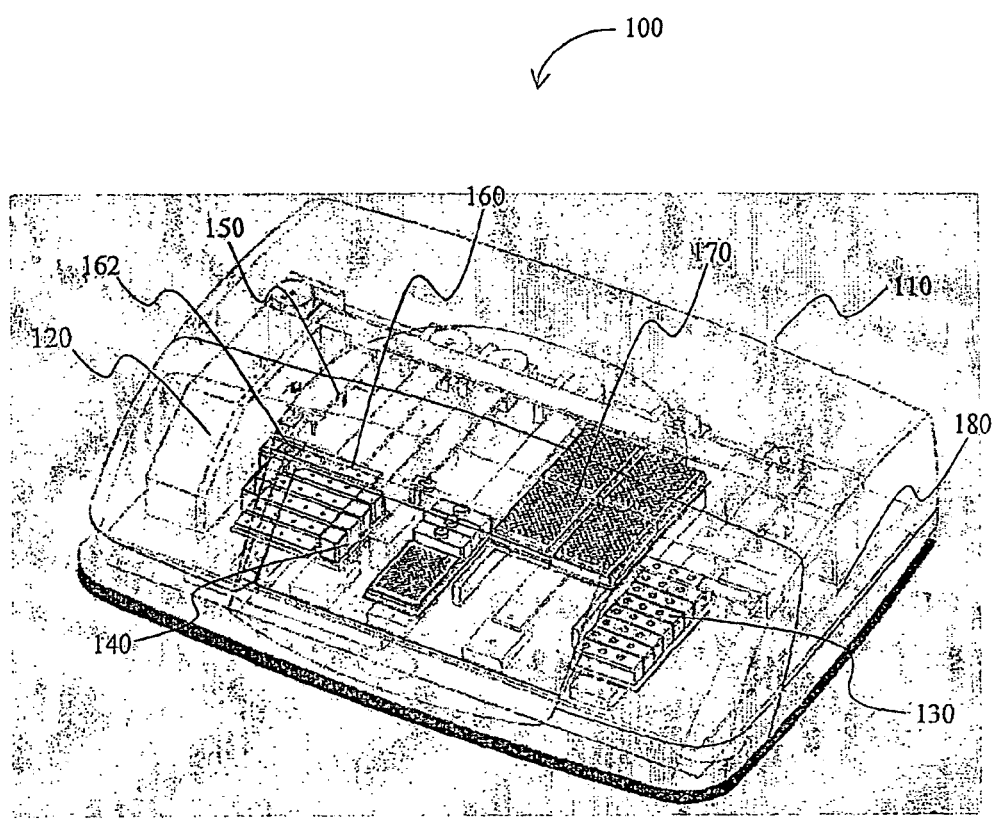
FIG. 1 is a schematic view of an exemplary analytic device according to the inventive subject matter.

As used herein, the term "desktop analytic device" refers to an integrated apparatus in which a housing at least partially, and more typically entirely encloses at least a detector and a fluidics station, and wherein the apparatus is portable as a single piece of equipment from one location to another location. Particularly preferred dimensions for contemplated desktop analytic devices will allow placement of the device on top of a standard sized laboratory bench. Therefore, a device that includes within a housing (e.g., 40 inches width× 30 inches depth×20 inches height) a detector, a fluidics station, a sample holder (e.g., a multi-well plate), a multi-biochip magazine, and a multi-reagent pack is considered a desktop analytic device under the scope of this definition, while an assembly of a robotic arm, a fluidics station, and a multi-well plate reader on a mounting platform is not considered a desktop analytic device under the scope of this definition.

As further used herein, the term "fluidics station" refers to a subsystem of an analytic device, wherein the subsystem is configured to receive (and preferably retain) a biochip, and wherein a fluid dispensing mechanism (e.g., automated pipette, tubing, etc) provides and/or removes fluid to and/or from the biochip while the biochip is disposed on a platform. Particularly preferred platforms generally include a flat surface, optionally comprising a retaining and/or guiding structure for the biochip, wherein the term "substantially horizontal" means that the platform forms an angle with an absolute horizontal of no more than 15 degrees.

As used herein, the term "biochip" generally refers to a carrier that has a plurality of probes (to which an analyte may be coupled) in predetermined positions. In especially preferred biochips, at least one of the probes is coupled to the carrier via a crosslinker that is disposed in a matrix, and exemplary multi-substrate biochips are described in commonly-owned and copending U.S. patent application Ser. No. 10/346,879, filed Jan. 17, 2003, and the PCT applications with the Ser. No. PCT/US02/03917, filed Jan. 24, 2002, and PCT/US01/47991, filed Dec. 11, 2001, all of which are incorporated by reference herein. However, it should be especially noted that the term "biochip" and "biochip-containing device" specifically excludes a multi-well plate.

The term "predetermined position" of an analyte refers to a particular position of the analyte on the chip that is addressable by at least two coordinates relative to a registration marker on the chip, and particularly excludes a substantially complete coating of the chip with the analyte an/or probe. Therefore, preferred pluralities of predetermined positions will include an array with a multiple rows of substrates forming multiple columns. As further used herein the term "registration marker" refers to a marker on the biochip that is used to provide a reference point for a position of an analyte. In especially preferred aspects, the registration marker is optically detectable and comprises a fluorescent dye, a luminescent, light-absorbing, and/or light-reflective compound, wherein illumination of the registration marker is most preferably performed at a wavelength that is not absorbed by the label of the analyte.

As further used herein, the term "probe" generally refers to any molecule, complex of molecules, or cell that binds to an analyte with a dissociation constant $K_D \leq 10^{-2}M$, and more typically $K_D \leq 10^{-3}M$, at a temperature of 25° C. and physiological buffer conditions (e.g., pH between 6.5 and 8.5, and ionic strength sufficient to maintain native conformation, viability, and/or Watson-Crick hybridization (between ligand and anti-ligand) of the anti-ligand). Thus, suitable probes include nucleic acids (and their analogs), polypeptides, lipids, macromolecular complexes of nucleic acids, polypeptides, carbohydrates, and lipids, as well as viruses, bacteria and/or eukaryotic cells. In further preferred aspects, it should also be appreciated that the probe may further include a label. For example, where a probe on the biochip may include a fluorescent label, wherein the fluorescence is quenched by a molecule that binds to the probe. Alternatively, a probe may also include an optically detectable label (e.g. for calibration of a signal in a quantitative assay).

Similarly, the term "analyte" as used herein refers to any molecule, complex of molecules, or cell that binds to the probe with a dissociation constant of $K_D \leq 10^{-2}M$ and more typically $K_D \leq 10^{-3}M$, at a temperature of 25° C. and physiological buffer conditions (i.e., pH between 6.5 and 8.5, and ionic strength sufficient to maintain native conformation, viability, and/or Watson-Crick hybridization (between ligand and anti-ligand) of the anti-ligand). Therefore, suitable analytes include nucleic acids (and their analogs), polypeptides, lipids, metabolites, hormones, macromolecular complexes of nucleic acids, polypeptides, carbohydrates, and lipids, as well as viruses, bacteria and/or eukaryotic cells. Still further, it should be understood that the analyte may include an optically detectable label, which may be naturally present in the analyte, or coupled to the analyte before, during or after binding of the analyte to the probe. Particularly contemplated labels include light-absorbing compounds, fluorescent labels, phosphorescent labels, and luminescent labels that produce an analyte signal where the label is coupled to the analyte. Contemplated analyte signals therefore include a fluorescence signal, a chemiluminescence signal, or a phosphorescence signal. Thus, it should be recognized that a probe and an analyte form an optically detectable binding pair, wherein the analyte is optically detected via the label.

As still further used herein, the term biochip is moved/transported "without manual intervention of an operator" means that actuation of the biochip occurs without the operator physically touching (e.g., manually gripping or lifting) the biochip, however, does not exclude manual programming (e.g., typing on a keyboard or touch screen) of the analytic device to effect automatic movement of the biochip.

More particularly, as shown in FIG. 1, an exemplary desktop analytic device 100 includes a housing 110 that encloses a confocal microscope detector 120 that is coupled to a sample processing platform 160 via pathway 162. The sample processing platform 160 includes an energy source (e.g., Peltier element, not shown), and abuttingly coupled to the sample processing platform 160 is multi-biochip magazine 140 that provides one or more biochips (not shown) to the platform 160. The biochips are moved from the magazine to the platform, and from the platform to the detector via actuator 150, wherein the robotic arm that includes the actuator 150 further includes an automatic pipette (not shown). Sample station 170 includes multi-well plates from which the automatic pipette transfers sample fluid to the biochip. Multi-reagent packs 130 provide the required reagents for reaction and other processing steps of the sample in the biochip. A data transfer interface 180 provides data connectivity to a computer located outside of the housing 110.

Figure 2:
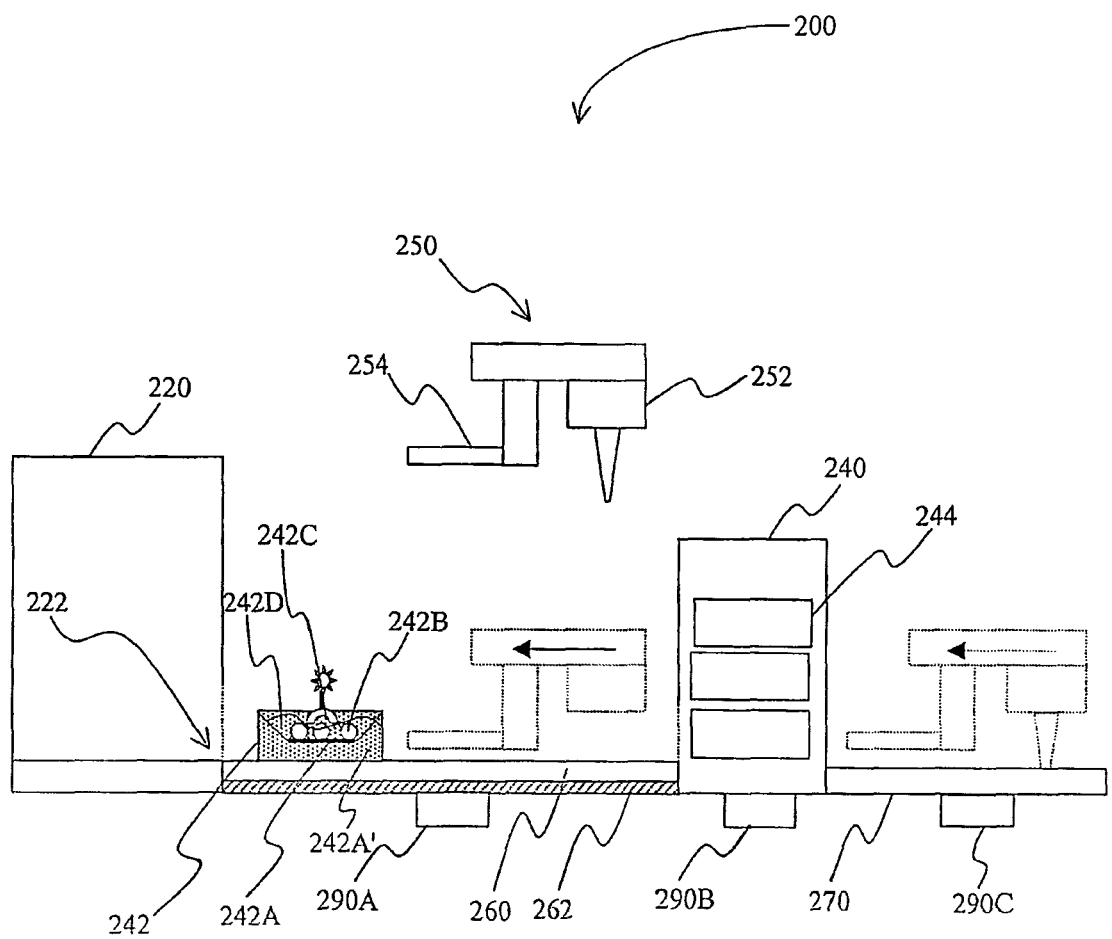
FIG. 2 is a schematic view of an exemplary sample processing platform that is coupled to a confocal microscope detector according to the inventive subject matter.

Therefore, in an especially preferred aspect of contemplated desktop analytic devices, a sample processing platform is operationally coupled to at least a confocal microscope detector and a biochip magazine as schematically depicted in exemplary configuration 200 of FIG. 2. Here, the confocal microscope detector 220 is abuttingly coupled to the sample processing platform 260 (which is coupled to Peltier element 262) to form substantially horizontal transport path 222 for the biochip-containing device 242. Biochip-containing device 242 includes biochip 242A that is coupled to housing 242A', wherein housing 242A' retains fluid 242D from which analyte 242C is bound to probe 242B (which is coupled to the biochip).

Actuator 250 comprises manipulator arm 254 (which is most preferably movable coupled to the actuator, wherein the arm may be rotated about its longitudinal axis and/or extended from the actuator 250) and automatic pipette 252. When the biochip-containing device 242 is moved from the platform to the detector, actuator 250 (or manipulator arm 254) descends to the biochip-containing device 242 and pushes the device into a suitable opening of the detector 220 (see actuator in dotted lines and dotted opening). Where desired, additional actuator mechanism 290A may move the sample processing platform along at least one coordinate (preferably along a coordinate other than the movement of the device 242).

Multi-biochip magazine 240 provides a plurality of additional devices 244 to the analyzer, wherein the actuator 250 (or manipulator arm 254) pushes the device 244 from one side of the magazine to the platform as indicated by the dotted rendition of the actuator to the right of the magazine. Depending on the size and position of the sample processing platform, it should be recognized that multiple devices 242 may be present on the platform 260. Similarly to the movement of the platform, it is also contemplated that the magazine may be translated along at least one coordinate using magazine actuator mechanism 290B (and preferably along a coordinate other than the movement of the device 242). While the magazine is depicted in FIG. 2 to be abuttingly coupled to the platform 260, it is also contemplated that a separate transfer path (e.g., small non-movable platform abuttingly coupled to both the platform and the magazine) may be interposed between the magazine and the platform. Alternatively, or additionally a separate transfer path (e.g., small non-movable platform abuttingly coupled to both the platform and the detector) may be interposed between the magazine and the detector.

Sample fluid may be provided from a multi-well plate 270, which may also be movable in the analytic device via actuator mechanism 290C and/or reagents may be provided from a multi-reagent pack (not shown), which may also be movable in the analytic device via actuator mechanism 290C. Removal and/or transfer of fluids and/or reagents to and from the device 242 is preferably performed using the automatic pipette 252.

With respect to the detector, it is particularly preferred that the detector comprises a confocal and/or dark field microscope, and particularly suitable detectors are described in our commonly owned and copending application with the title "Microarray Detector and Methods", filed on May 28, 2003, which is incorporated by reference herein. However, it should be recognized that all known optical detectors are also suitable for use herein so long as a biochip can be moved along a substantially horizontal transport path between the platform and the detector. It is further contemplated that suitable detectors may have an opening that can be sealed to prevent stray light from interfering with a test performed in the detector. Such sealing is preferably achieved with a slidable or otherwise moving door, but is not necessarily limiting to the inventive concept presented herein.

Furthermore, it is generally preferred that the detector temporarily or permanently forms a substantially horizontal transport path with the platform by abutting with at least part of the platform. Alternatively, in a less preferred aspect, the platform may be moved towards the detector to abut with the detector, thereby forming a transport path for the biochip. Where temporary or permanent direct coupling of the detector to the platform is not desired, it is contemplated that a separate substantially horizontal intermediate platform may be included wherein the intermediate platform is (at least temporarily) coupled to the detector and/or the sample processing platform. The biochip is preferably retained (relative to at least one coordinate) in the detector via a retaining mechanism, and a particularly preferred retaining mechanism includes a guide rail that engages one (and more typically two sides) of a biochip (or a housing of the biochip).

Especially preferred biochips are those that comprise a plurality of probes (to which an analyte may be coupled) in predetermined positions. In especially preferred biochips, at least one of the probes is coupled to the carrier via a crosslinker that is disposed in a matrix, and exemplary multi-substrate biochips are described in commonly-owned and copending U.S. patent application Ser. No. 10/346,879, filed Jan. 17, 2003, and PCT application with the Ser. No. PCT/

US02/03917, filed Jan. 24, 2002. In further preferred aspects of the inventive subject matter, the biochip is disposed in a housing and exemplary biochip-containing devices are described in our commonly owned copending PCT application with the Ser. No. PCT/US01/47991, which was filed Dec. 11, 2001. Still further, and especially where binding of the analyte or removal of non-specific analytes requires a heating step, it is contemplated that the housing of the biochip includes a base that is thermally conductive (e.g., metal base, or includes metal filings in a polymeric base).

However, in alternative aspects, contemplated biochips and/or biochip-containing devices may be modified and all of such alternative biochips are deemed suitable for use herein. For example, where a biochip is disposed in a housing, the housing may include a movable cover, various fluid channels for addition and/or removal of fluids, optical implements, and/or other elements that will directly or indirectly interact with the fluid, analyte, and/or probe. In another example, where a biochip has no housing, it is contemplated that the biochip may include a base or other element that engages with a biochip guiding structure in the platform and/or detector. With respect to contemplated analytes and probes for a biochip used in conjunction with the teachings presented herein, the same considerations as provided in the definition for the terms "analyte" and "probe" apply. Therefore, suitable biochips will generally include a plurality (e.g., between 25 and several hundred) of probes in predetermined positions, wherein one or more of the probes may bind an analyte from a sample fluid (e.g., biological fluid of a patient) comprising a plurality of non-analytes. Consequently, the biochip will be at least in part immersed in a fluid (e.g., sample fluid, hybridization or binding buffer, or wash fluid, preferably retained by the housing of the biochip) while the biochip is in the detector and/or in the sample processing platform, or while the biochip is moved from the sample processing platform to the detector.

Where multiple biochips are employed in a series of analytic procedures, it is still further preferred that at least some of the biochips may be disposed in a multi-biochip magazine, wherein the magazine is coupled to the sample processing platform. For example, the magazine may be directly and abuttingly coupled to the platform to form a substantially horizontal transfer path. On the other hand (e.g., where the magazine is relatively distantly positioned relative to the sample platform), a separate horizontal transfer path may be coupled to the magazine and the platform to ensure sliding transfer or other movement between the magazine and the platform. Thus, in one preferred aspect of the inventive subject matter, an actuator (infra) moves the biochip from the magazine to the platform.

With respect to the sample processing platform, it is generally preferred that the platform is configured such that the platform receives and at least temporarily retains a biochip from a location other than the platform. Consequently, suitable platforms will have a size that corresponds to at least the size of the biochip, and more typically to a multiple of the size of a biochip to accommodate more than one biochip at a time (e.g., where multiple samples are incubated at the same time before analysis). Furthermore, it is generally preferred that the platform has a guiding structure that provides guided movement of the biochip when the biochip is pushed by an actuator from one position to another position. For example, where the biochip has a housing with a base that protrudes from the perimeter of the housing, a suitable guiding structure may include an engaging rail along which the base of the biochip moves. In another example, where the biochip has no housing, the platform may also include a channel in which the biochip can move along one or two coordinates (i.e., x- and y-coordinate).

Depending on the particular actuator structure and/or spatial environment within the analytic device, it is contemplated that the platform may be in a fixed position or movable coupled to the housing. For example, where the actuator and/or platform is configured to enable movement of the biochip along x- and y-coordinate, the platform may be in a fixed position. On the other hand, and especially where multiple platforms are provided in the analytic device, it is contemplated that the platform is movably coupled relative to the detector. Especially preferred manners of movably coupling include those in which a motor (e.g., stepper, piezo, linear, or other electromotor) actuates the platform(s) in a linear motion along at least one coordinate. For example, where an actuator moves a biochip along the x-coordinate, it is preferred that a motor actuates the platform along the y-coordinate.

Contemplated sample processing platforms are generally substantially horizontal and are functionally coupled to an energy source that provides energy to the fluid in the biochip. For example, where thermal energy is employed to control hybridization stringency in a nucleic acid binding assay, the energy source may advantageously include a heater and/or a cooling element, which may be separately coupled to the platform or combined (e.g., as a Peltier element). In another example, where non-specific binding of non-analytes to one or more probes is problematic, an ultrasound transducer may provide ultrasound energy to disrupt such non-specific binding. Further contemplated energy sources include light energy sources (e.g., to destroy a photolabile compound), radiation energy sources, and all reasonable combinations thereof.

Consequently, functional coupling of the energy source will typically depend at least in part on the particular energy source. For example, where the energy source is a heater and/or cooler, physical coupling to the platform is generally preferred. On the other hand, where the energy source is a radiation (visible or electromagnetic), indirect coupling may be suitable by directing a beam of radiation to the fluid and/or biochip. In another example, where ultrasound energy is delivered to the fluid, the transducer may be coupled to the platform or may be inserted (e.g., via a transducer tip) into the fluid (e.g., using the actuator). Appropriate energy levels will generally depend on the nature of the energy source, and it is contemplated that suitable energy levels will be in the range of several mW to several W (e.g., to create a photoradical, or to heat the fluid from 25 centigrade to 45 centigrade).

Particularly preferred actuators in contemplated desktop analytic devices comprise a robotic arm that moves along one coordinate (e.g., x-coordinate) and that further includes an additional functional element that moves along at least one other coordinate (e.g., y-, and/or z-coordinate). For example, preferred actuators may include a manipulator arm which may be moved in a rotational and/or translational (e.g., front-to-back, or side-to-side) movement. Such movement may be employed to impart a sliding movement to the biochip that may be disposed on the sample processing platform (e.g., to move the biochip from the platform to the detector via the transfer path, or to move the biochip from the magazine to the platform via another transfer path). Thus, it should be recognized that movement of the biochip from the platform to the detector may be caused by an actuator that pushes the biochip along at least one of an x-coordinate and a y-coordinate. Actuator-based movement of the biochip may further be employed to move the biochip among numerous alternative locations within the desktop analytic device, and particularly contemplated alternative movements include sliding movements from a multi-biochip magazine to the sample processing platform (using the same of a different actuator without manual operation intervention). Alternatively, or additionally contemplated actuators will also include an automatic pipette that transfers liquid from one location to another (e.g., from a multi-reagent pack to the biochip, or from a sample reservoir to the biochip) within the desktop analytic device.

Of course, it should be recognized that the actuator may have various alternative 110 configurations so long as the actuator still provides movement (most preferably sliding movement) to the biochip. For example, suitable actuators may include those in which a robotic arm moves along two coordinates (e.g., x-, and y-coordinate) and that further includes an additional functional element that moves along at least one other coordinate (e.g., y-, and/or z-coordinate). In still further contemplated examples, the actuator may also include a robotic arm that moves along three coordinates in translational and/or rotational motion. Less preferred (but not excluded) actuators will include actuators that lift the biochip from a first position to a second position. However, such lift actuators may cause undesirable misalignments between the biochip and another structure (e.g., the platform and/or the detector) with in the desktop analytic device and may therefore lead to improper or even missing test data. Therefore, it should be especially recognized that the biochip is moved within contemplated desktop analytic devices without manual intervention of an operator from a first location to a second location, and more preferably from the sample processing platform (fluidics station) to the detector while one or more analytes are bound to the biochip.

Contemplated desktop analytic devices may advantageously include a data transfer interface that is electronically coupled to one or more components of the analytic device, and especially contemplated components include a computer that controls operation of the analytic device (and may further provide test data analysis), the detector, and the sample processing platform. Such data transfer interfaces (e.g., telephonic, DSL, or cable modem) may transfer operational parameters from the component to another computer to provide status information or troubleshooting guidance for the desktop analytic device, or to provide access to remote operation. For example, the sample processing platform may include various sensors that provide feedback on operating condition, number of biochips, environmental parameters, etc. to generate a status code (e.g., incubation in progress, over-temperature alarm, etc.) that may then be transferred to the operator of the analytic device as well as to a person other than the operator, which may be in a remote location relative to the analytic device (e.g., at a different ZIP code, different city, county, or even state).

Therefore, the inventors particularly contemplate a desktop analytic device having a substantially horizontal sample processing platform that receives a biochip that is at least partially enclosed in a housing, wherein the biochip is at least partially immersed by a fluid that is retained by the housing, wherein the biochip binds an analyte from the fluid, and wherein the fluid further comprises a non-analyte. An energy source is functionally coupled to the platform and delivers energy to the fluid in the biochip, and confocal microscope detector is coupled to the platform such that a substantially horizontal transport path is formed between the detector and the platform, wherein the biochip is moved in a sliding motion from the platform to the detector via the transport path. In such devices, it is generally preferred that the biochip is moved within the desktop analytic device without manual intervention of an operator from the platform to the detector while the analyte is bound to the biochip, wherein the sample processing platform and the detector are enclosed in the desktop analytic device.

Viewed from another perspective, it should be recognized that contemplated desktop analytic devices include a multi-biochip magazine, a fluidics station with a sample processing platform, and confocal microscope detector, wherein a biochip is moved from the magazine via the sample processing platform to the detector without manual intervention of an operator.

With respect to movements in such devices, it is typically preferred that at least one of the multi-biochip magazine and the stringency platform move along a x-coordinate while the biochip is moved along a y-coordinate, and/or that the fluidics station comprises an automatic pipette disposed within the device, wherein the pipette moves along at least one of an x-coordinate, a y-coordinate, and a z-coordinate. In further preferred aspects, the multi-biochip magazine and/or the stringency platform are actuated by a stepper motor, piezo motor, or a linear motor, wherein the biochip is actuated by an actuator that pushes the biochip along at least one of an x-coordinate and a y-coordinate (preferably, the biochip is moved while the biochip is at least partially immersed in a fluid).

Furthermore, it is generally contemplated that in some aspects of the inventive subject matter the stringency platform and the confocal microscope detector are coupled to each other such that a portion of the stringency platform and a portion of the confocal microscope detector abut each other to form a transport path. Alternatively, or additionally, the stringency platform and the multi-biochip magazine may be coupled to each other such that a portion of the stringency platform and a portion of the multi-biochip magazine abut each other to form another transport path.

Further contemplated analytic devices may further include a multi-reagent pack and an automated pipettor to form an integrated analytic device. Particularly preferred automatic pipettors contemplated in conjunction with the teachings presented herein include those described in our co-pending international patent application with the title "Level-Controlled Pipette For Automated Analytic Devices", filed May, 28, 2003, which is incorporated by reference herein. Particularly preferred multi-reagent packs contemplated in conjunction with the teachings presented herein include those described in our co-pending international patent application with the title "Multi-Reagent Pack", filed May, 28, 2003, which is incorporated by reference herein.

Thus, specific embodiments and applications of integrated desktop analytic devices with sample processing platforms have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A desktop analytic device that comprises:
a substantially horizontal sample processing platform that is configured to receive a biochip, wherein the biochip is at least partially enclosed in a housing, wherein the housing is configured to allow at least partial immersion of the biochip by a fluid that is retained by the housing;

an energy source that is thermally and mechanically coupled to the platform and configured to allow delivery of energy from the platform through the housing to the fluid in the biochip while the biochip is disposed on the platform;

a confocal microscope detector that is coupled to the platform such that a substantially horizontal transport path is formed between the detector and the platform, a push actuator operationally coupled to a robotic arm, wherein the robotic arm and the push actuator are configured to allow pushing of the biochip along a y-coordinate in a sliding motion from the platform into the detector via the transport path;

a magazine that is configured to hold a plurality of biochips;

wherein the robotic arm, the platform, and the detector are configured such that the biochip is movable by the actuator in a sliding motion within the desktop analytic device without manual intervention of an operator from the magazine to the platform, and from the platform to the detector while an analyte is bound to the biochip; and wherein the sample processing platform and the detector are enclosed in the desktop analytic device.

2. The desktop analytic device of claim 1 wherein the sample processing platform is configured to receive a second biochip while the biochip is disposed on the platform.

3. The desktop analytic device of claim 1 wherein the platform is configured to allow movement of the biochip from the platform to the detector while the biochip is at least partially immersed in the fluid.

4. The desktop analytic device of claim 1 wherein the energy source comprises at least one of a heater, a cooling element, and an ultrasound source.

5. The desktop analytic device of claim 1 wherein the biochip comprises a thermally conductive base that cooperates with the sample processing platform to transmit the energy from the sample processing platform to the biochip.

6. The desktop analytic device of claim 1 wherein the platform is configured to allow application of the fluid to the biochip from a sample reservoir located within the desktop analytic device while the biochip is disposed on the platform.

7. The desktop analytic device of claim 1 further comprising a data transfer interface that is configured to transfer data to a person other than the operator of the desktop analytic device.

8. The desktop analytic device of claim 7 wherein the data transfer interface is configured to allow informational coupling of the desktop analytic device to a person other than the operator in a remote location to thereby provide status information of the analytic device.

9. The desktop analytic device of claim 1, wherein the sample processing platform is configured to move in a motion other than along the y-coordinate.

* * * * *